(12) United States Patent
Venturelli (10) Patent No.: US 8,858,863 B2
(45) Date of Patent: Oct. 14, 2014

(54) BALLOON FOR THE TREATMENT OF STENOSIS AND METHOD FOR MANUFACTURING THE BALLOON

(75) Inventor: Andrea Venturelli, Brescia (IT)

(73) Assignee: Invatec S.p.a., Roncadelle, Brescia (IT)

( * ) Notice: Subject to any disclaimer, the term of this patent is extended or adjusted under 35 U.S.C. 154(b) by 1182 days.

(21) Appl. No.: 12/744,308

(22) PCT Filed: Nov. 21, 2007

(86) PCT No.: PCT/IT2007/000816
§ 371 (c)(1),
(2), (4) Date: May 21, 2010

(87) PCT Pub. No.: WO2009/066330
PCT Pub. Date: May 28, 2009

(65) Prior Publication Data
US 2012/0253380 A1    Oct. 4, 2012

(51) Int. Cl.
*A61M 25/00* (2006.01)
*B05D 3/00* (2006.01)
*A61M 31/00* (2006.01)
*A61M 37/00* (2006.01)
*B29C 49/00* (2006.01)
*A61F 2/958* (2013.01)
*A61M 25/10* (2013.01)

(52) U.S. Cl.
CPC .............. *A61M 25/104* (2013.01); *A61F 2/958* (2013.01); *A61M 2025/0057* (2013.01); *A61M 2025/1004* (2013.01); *A61M 25/1011* (2013.01); *A61M 2025/105* (2013.01); *A61M 25/1002* (2013.01)

USPC ...................... 264/534; 604/103.02; 427/2.28

(58) Field of Classification Search
USPC ............. 604/103.02, 103.04–103.08, 103.14; 427/2.28; 264/523, 531, 534, 573
See application file for complete search history.

(56) References Cited

U.S. PATENT DOCUMENTS

| 5,102,402 | A | 4/1992 | Dror et al. |
| 5,746,745 | A | 5/1998 | Abele et al. |
| 5,893,840 | A | 4/1999 | Hull et al. |
| 8,287,940 | B2 * | 10/2012 | Von Holst et al. ........... 427/2.28 |
| 2004/0068285 | A1 | 4/2004 | Burgmeier et al. |
| 2004/0215227 | A1 * | 10/2004 | McMorrow et al. .......... 606/191 |

FOREIGN PATENT DOCUMENTS

| WO | WO 97/31674 | 9/1997 |
| WO | WO 97/31674 A1 | 9/1997 |
| WO | WO 2005/023153 A2 | 3/2005 |
| WO | WO 2005023153 | 3/2005 |
| WO | WO 2007090385 A2 * | 8/2007 |

* cited by examiner

*Primary Examiner* — Nathan R Price (57) ABSTRACT

The present invention relates to a balloon (1) for treating stenosis and the method for obtaining this balloon. The method comprises the steps of: bringing the balloon in the deployed configuration; placing a plurality of stylets (17) that are arranged in the axial direction along the outer wall (10) of the balloon; pushing the stylets towards the balloon core (11) in the radial direction such as to form a plurality of laps (12); laying the laps about the core in the tangential direction such as to lay each lap on an adjacent stylet; removing the stylets such as to form a plurality of cavities (13) comprised between each lap and the balloon core; filling the cavities with the drug.

14 Claims, 6 Drawing Sheets

ARTE NOTA

BALLOON FOR THE TREATMENT OF STENOSIS AND METHOD FOR MANUFACTURING THE BALLOON

The present invention relates to a balloon and a catheter for angioplasty and pharmacologic treatment of stenosis. The invention further relates to a method for manufacturing the balloon and catheter.

Catheters for the angioplasty treatment of stenosis within the human body circulatory system have been known for a long time. These catheters comprise a balloon at the distal end thereof. The balloon is inserted within the blood vessels in a deflated configuration and is brought proximate to the stenosis, where it is inflated. Thereby, a mechanical treatment of the stenosis is obtained, which is suitable to restore the section of the blood vessel.

It has been recently noted that the effectiveness of this merely mechanical angioplasty operation results to be dramatically improved when a drug suitable to prevent restenosis is used in association therewith. Suitable drugs for this kind of treatment are anti-tumour drugs that are adapted to be used as antiproliferatives. These drugs can be, for example: Rapamycin, Epothilone, and mainly Paclitaxel.

Particularly, attempts have been made to coat the angioplasty balloon with a gelatinous layer consisting of a mixture of a suitable solvent and Paclitaxel. In the previous patent applications: WO 2004/028610, WO 2004/028582, and WO 2002/076509, of which the appointed inventor is Professor Ulrich Speck, has been described how a lipophilic drug, such as Paclitaxel, can be positioned on the outer portion of an angioplasty balloon.

This known method, however, is not without defects.

First of all, in order to reach the length that presents the stenosis, the balloon is required to travel along a relatively long pathway within the healthy blood vessels. Along this pathway, the drug is very likely to be partially removed due to friction against the healthy vessel walls.

This determines some undesirable consequences. First, it determines the administration of an amount of drug near the stenosis which is lower than expected and a priori unknown. Secondly, it determines the dispersion of a powerful drug in healthy districts of the body, with consequent undesirable secondary effects. Thirdly, it has been noted that after the drug has been carried proximate to the stenosis, this can be immediately dispersed immediately after normal blood flow has been restored.

The object of the present invention is to provide an angioplasty balloon, the catheter thereof and the method for manufacturing the same, which allow at least partially overcoming the drawbacks mentioned above with reference to the prior art.

More particularly, the task of the present invention is to provide an angioplasty balloon which allows administering all the drug provided thereon in the stenosis area upon being introduced within the patient's body.

A further task of the present invention is to provide an angioplasty balloon, which restrains the dispersion of the drug in healthy districts of the patient's body.

The task of the present invention is further to provide an angioplasty device which restrains the dispersion of the drug after it has been released, thereby preventing the washing effect that commonly occurs when the normal blood flow has been restored.

This object and these tasks are achieved by an angioplasty balloon in accordance with claim 1, a catheter in accordance with claim 23 and a method for manufacturing the balloon in accordance with claim 25.

Further features and advantages of the present invention will be better understood from the description of some exemplary embodiments, which is given below by way of non-limiting illustration, with reference to the following figures:

FIG. 4a to 4d are front views of an angioplasty balloon during subsequent steps of the method according to the invention;

FIG. 6a to 6d are different possible sections of the stylet shown in FIG. 5;

With reference to the figures, with 1 has been designated an angioplasty balloon that is mounted at the distal end of a catheter 2.

The catheter 2 further comprises, in a manner known per se, an elongated tubular body 3 that is provided with a plurality of lumens 4, and of a connector 5 at the proximal end thereof.

The balloon 1, in a manner known per se, is suitable to alternatively adopt a deployed configuration and a collapsed configuration. The balloon is brought to the deployed configuration by means of the injection of a pressurized inflating liquid, and vice versa, is brought to the collapsed configuration by means of the suction of the inflating liquid.

The balloon is suitable, in the collapsed configuration, to be inserted within the circulatory system of a patient's body and to be advanced along the vessels to reach a vessel section that is affected by stenosis. The balloon 1 is further suitable to apply, when it passes from the collapsed configuration to the deployed configuration, a radial force to the stenosis such as to expand the latter and restore the nominal section of the vessel.

The balloon 1 comprises an outer wall 10 and a core 11 matching with the distal end of the catheter 2. The core 11 defines an axis X about which the balloon 1 is developed.

By the term "axial" below is meant the direction of a straight line parallel to the axis X. By the term "radial" below is meant the direction of a half-line originating on the axis X and perpendicular thereto. Finally, by the term "circumferential" (or "tangential") is meant below the direction of a circumference (or tangent thereof) that is centered on the axis X and lying on a plane perpendicular to the axis X.

Figure 1:
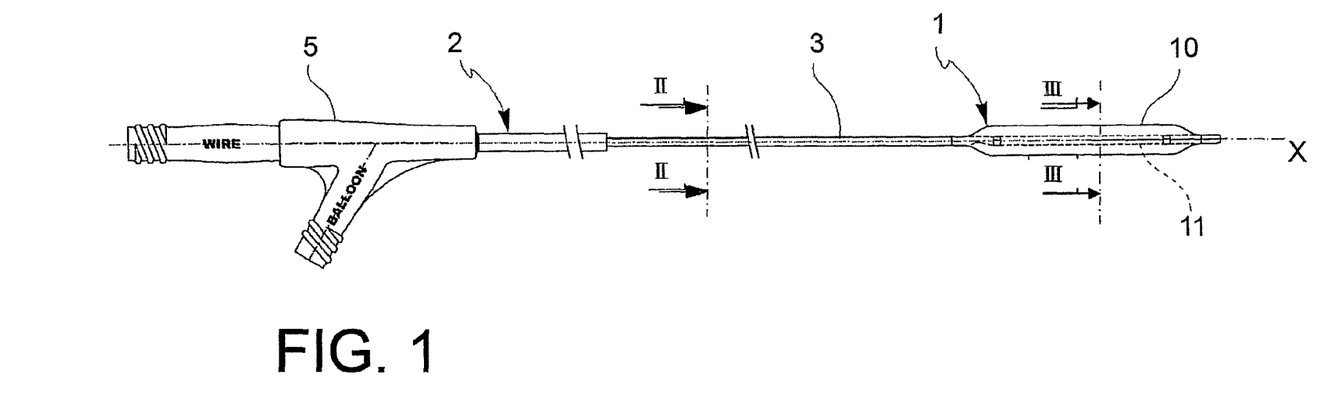
FIG. 1 is a side view of an angioplasty catheter of the prior art.
Figure 2:
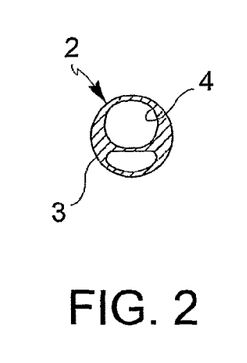
FIG. 2 is the section along the line II-II in FIG. 1.
Figure 3A:
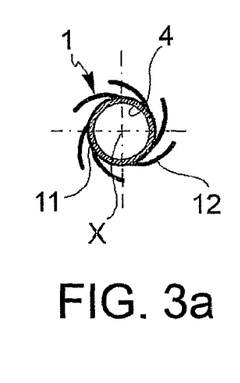
FIG. 3a is a possible section along the line III-III in FIG. 1.
Figure 3B:
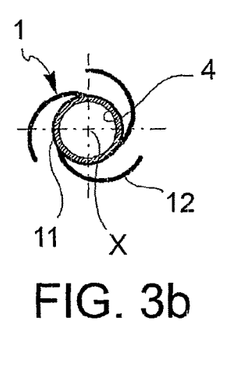
FIG. 3b is another possible section along the line III-III in FIG. 1.
Figure 4:
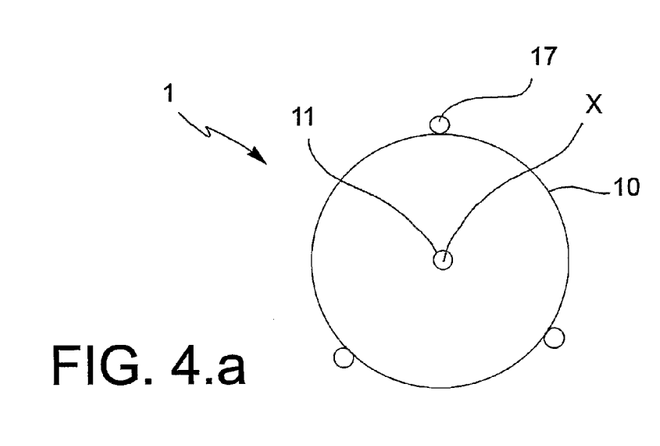
Figure 7:
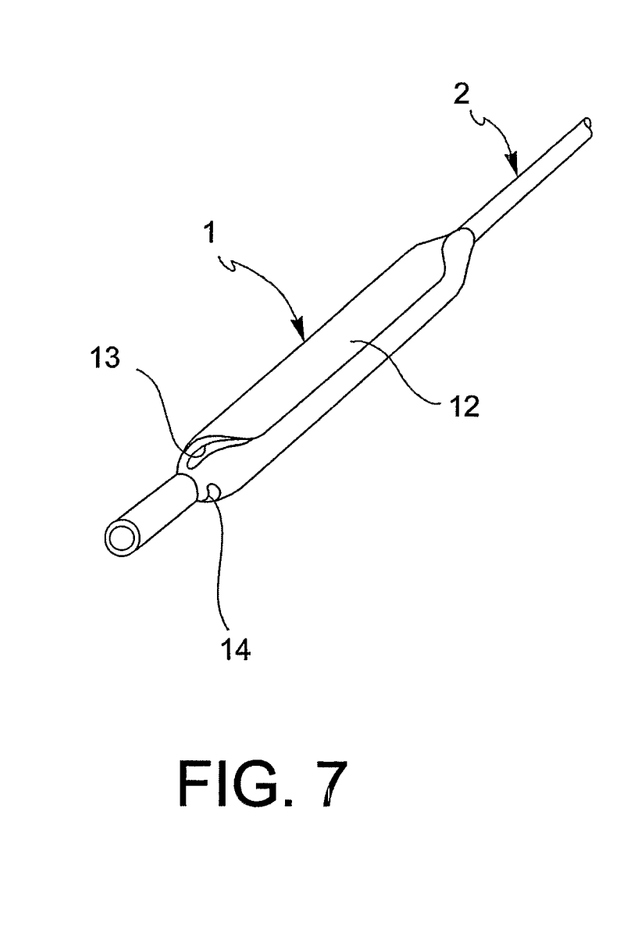
FIG. 7 is a perspective view of the balloon according to the invention in a collapsed configuration.

In the collapsed configuration, the balloon 1 according to the invention (see FIGS. 4d and 7) comprises a plurality of laps 12 that are laid about the core 11 in the circumferential direction. Each of the laps 12 is laid such as to provide a cavity 13 comprised between the lap and the core 11. The cavities 13 are filled with a drug 14.

Figure 8:
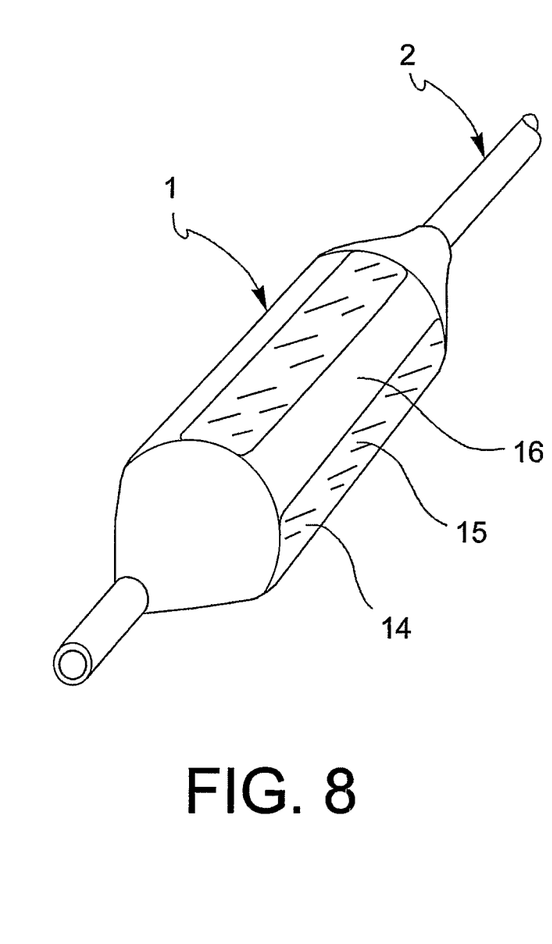
FIG. 8 is a perspective view of the balloon according to the invention in a deployed configuration.

In the deployed configuration, the balloon 1 according to the invention (see FIG. 8) comprises a plurality of bands 15 of drug 14 that are axially arranged along the outer wall 10. The bands 15 of drug 14 are alternated in the circumferential direction with strips 16 in which the drug 14 is not provided and the outer wall 10 is directly exposed.

The number of bands 15, and consequently the number of strips 16, are linked to the number of laps 12. For example, the presence of three laps 12 when the balloon is in the collapsed configuration, determines the presence of three bands 15 of drug 14 that are alternated with as many cleaned strips 16.

In accordance with an embodiment, the bands 15 of drug 14 are wide about twice the strips 16.

The bands 15 are preferably equally spaced relative to each other in a circumferential direction along the outer wall 10 of the balloon 1.

In accordance with an embodiment of the invention, the balloon 1 comprises three laps 12. In accordance with other possible embodiments, the laps 12 can be provided in a different number in order to meet particular requirements.

In accordance with an embodiment of the balloon, the drug 14 comprises the Paclitaxel as the active ingredient. The Paclitaxel is available with the trade name of Taxol®, which is a registered mark of Bristol-Myers Squibb.

In accordance with other embodiments, the drug 14 comprises other anti-tumour active ingredients that are suitable to be employed as antiproliferatives, such as: Rapamycin or Epothilone.

In accordance with an embodiment, the drug 14 comprises the active ingredient and a suitable excipient, for example a gel or a paste being suitable to penetrate within the cavities 13 and adhere to the wall 10 of the balloon 1.

In accordance with several possible embodiments of the invention, the balloon 1 according to the invention comprises containment means 20 to be capable of stopping the blood flow in the length in which the angioplasty operation has to be carried out.

The containment means 20 allow avoiding the washing effect in the blood flow which tends to remove and disperse the drug 14 immediately after the application by means of the balloon 1. In other words, as the blood flow is temporary stopped, the lipophilic drug can take the time required for linkage to the vessel walls. A dramatically lower washing effect occurs during the subsequent restoration of the flow.

Figure 9:
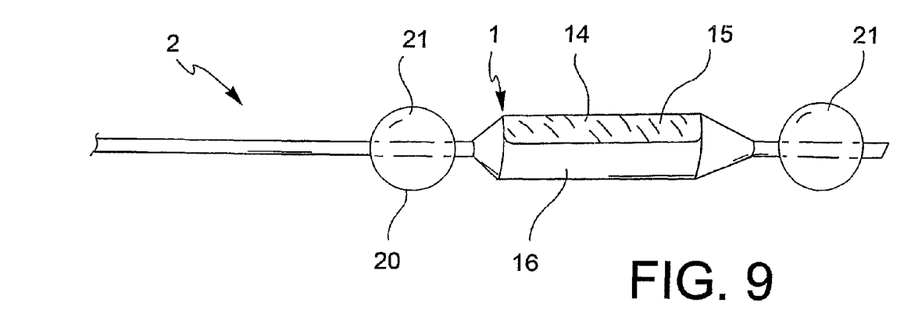
FIG. 9 is a side view of a balloon according to the invention in a deployed configuration.

In accordance with the embodiment depicted in FIG. 9, the containment means 20 comprise two auxiliary balloons 21 that are located at immediately proximal and immediately distal positions relative to the balloon 1.

Figure 11:
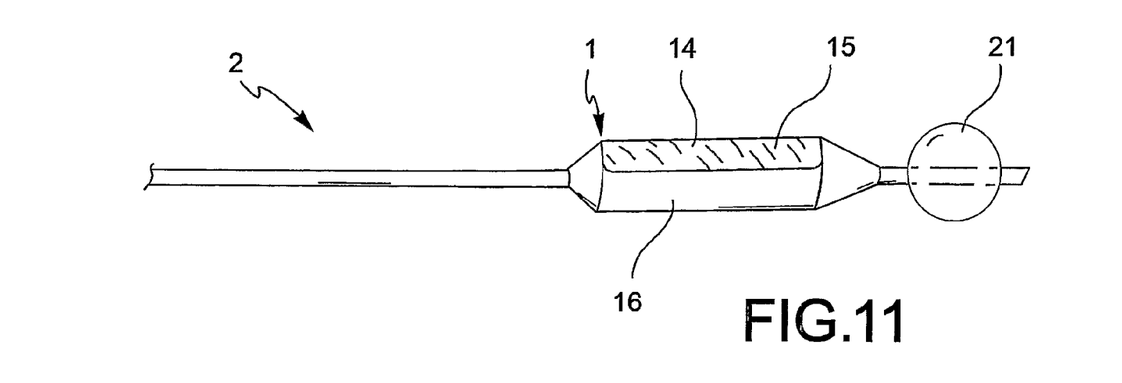
FIG. 11 is a side view of a balloon according to the invention in a deployed configuration.

In accordance with the embodiment depicted in FIG. 11, the containment means 20 comprise an individual auxiliary balloon 21 which is located at an immediately distal position relative to the balloon 1.

The auxiliary balloons 21 are suitable to pass from a collapsed configuration, in which they have minimum radial overall dimensions, to an deployed configuration (illustrated in FIGS. 9 and 11) in which they are suitable to come in contact with the walls of the blood vessel such as to stop the flow.

In accordance with an embodiment, the auxiliary balloons 21 are different from the balloon 1 in that they consist of an elastic wall and are not suitable to apply the radial force that is required for the angioplasty operation.

In accordance with an embodiment, the catheter 2 comprises an inflation/deflation duct for the balloon 1 and an individual inflation/deflation duct for the auxiliary balloons 21, even when two of them are provided. In accordance with another embodiment, the catheter 2 comprises an inflation/deflation duct for the balloon 1 and an inflation/deflation duct for each of the auxiliary balloons 21.

In the description of the procedure for using the catheters of FIGS. 9 and 11, reference is made to the auxiliary balloons 21, obviously considering also the case in which only one auxiliary balloon 21 is provided. The procedure for using the balloon 1 provides:
- inserting the catheter 2 within the site to be treated;
- bringing the auxiliary balloons 21 from the collapsed configuration to the deployed configuration;
- bringing the balloon 1 from the collapsed configuration to the deployed configuration such as to carry out the angioplasty operation and the deposition of the drug on the vessel walls;
- bringing the balloon 1 from the deployed configuration to the collapsed configuration;
- after a reasonable time (for example a few seconds), bringing the auxiliary balloons 21 from the deployed configuration to the collapsed configuration;
- removing the catheter.

In accordance with the embodiment as depicted in FIGS. 10a and 10b, the containment means 20 comprise two shaped portions 22 of the balloon 1. The shaped portions 22 are obtained as one piece with the balloon 1 and are placed at the ends, respectively distal and proximal, of the balloon 1.

Figure 10:
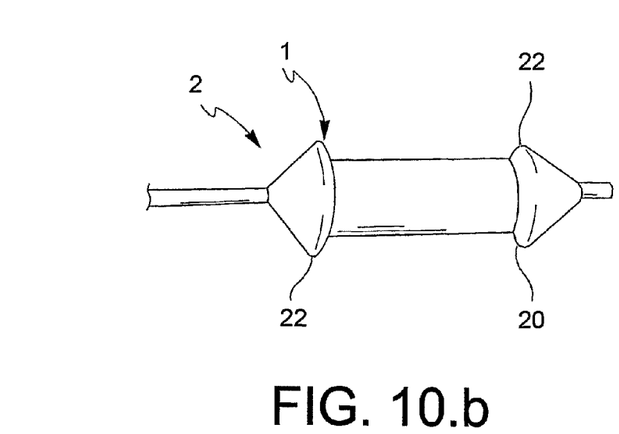
FIG. 10a is a side view of a balloon according to the invention in a semi-deployed configuration.
FIG. 10b shows the balloon in FIG. 10a in a deployed configuration.

The balloon 1 in FIG. 10 is capable of adopting three configurations:
- a collapsed configuration (non illustrated), in which it has minimum radial overall dimensions;
- a deployed configuration (FIG. 10a), in which it has maximum radial overall dimensions, and is capable of applying a radial force that is sufficient to bring the angioplasty operation to completion;
- a semi-deployed configuration (FIG. 10b) wherein the shaped portions 22 maintain the maximum radial overall dimensions, whereas the central length of the balloon adopts intermediate radial overall dimensions.

In accordance with an embodiment, the deployed configuration of the balloon 1 is obtained by means of a first level of internal pressure, whereas the semi-deployed configuration is obtained with a second level of internal pressure. The first level of pressure can be for example equal to about 14 bars, whereas the second level of pressure can be for example equal to about 7 bars.

The procedure for using the balloon 1 in FIG. 10 provides:
- inserting the catheter 2 within the site to be treated;
- bringing the balloon 1 from the collapsed configuration to the deployed configuration such as to carry out the angioplasty operation and the deposition of the drug on the vessel walls;
- bringing the balloon 1 from the deployed configuration to the semi-deployed configuration;
- after a reasonable time (for example a few seconds), bringing the balloons 1 from the semi-deployed configuration to the collapsed configuration;
- removing the catheter 2.

In accordance with the embodiment in FIG. 10, the catheter 2 comprises an individual inflation/deflation lumen for the balloon 1 and shaped portions 22.

In accordance with an embodiment of the invention, an angioplasty stent 6 is also fitted on the balloon 1. The stent 6, in a manner known per se, has a tubular structure that can alternatively adopt a collapsed configuration and a deployed configuration, similarly as the balloon 1.

Figure 12:
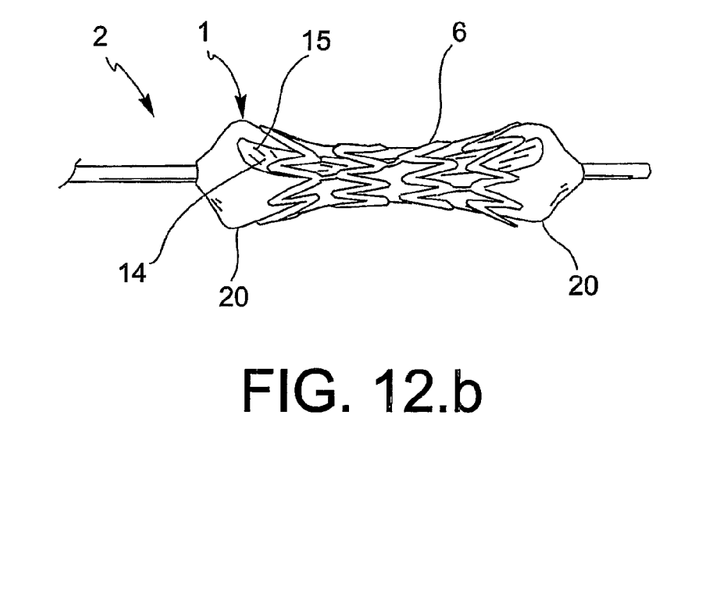
FIG. 12a is a side view of a balloon according to the invention in a collapsed configuration.
FIG. 12b shows the balloon in FIG. 12a in a semi-deployed configuration.

FIG. 12a schematically illustrates a balloon 1 according to the invention comprising a stent 6. The balloon 1 and the stent 6 are both in a collapsed configuration, and the stent 6 is either fitted or firmly wrapped onto the balloon 1. In this configuration, the stent 6 is capable of maintaining the laps 12 in position, such that they are not lifted and the drug 14 does not escape from the cavities 13.

The provision of the stent 6, in addition to meeting particular therapeutic requirements, can result particularly advantageous also when the pathway within the patient's blood vessels is particularly tortuous. In fact, when the balloon 1 is required to perform a curve with a small curvature radius (for example in the order of half the length of the balloon or less) the curvature imposed to the balloon 1 can cause one or more laps 12 to be lifted. The provision of the stent 6, on the contrary, avoids this risk, by setting a radial constraint upon the laps 12.

Furthermore, the presence of the stent 6 varies the inflating mode of the balloon 1, i.e., the presence of the stent 6 influences the mode in which the balloon 1 moves from the collapsed configuration to the deployed configuration. In fact, during the inflation of the balloon 1 without stent 6, the diameter of the balloon increases in a quite even manner along the axis X. The balloon 1 passes from the collapsed configuration (see for example FIG. 7) to the deployed configuration (see for example FIG. 8) while maintaining a substantially rectilinear profile of the central part of wall 10.

When the balloon 1 that is wrapped within the stent is being inflated, the diameter of the balloon increases, this time in an uneven manner, along the axis X. At the ends of the balloon 1, the radial resistance of the stent 6 is more easily overcome by the pressure applied within the balloon 1. Due to this fact, in a semi-deployed configuration, the assembly consisting of the balloon 1 and stent 6 temporarily adopts the shape as outlined in FIG. 12b. As may be noted, in this semi-deployed configuration, the central length of the wall 10 of balloon 1 is curved, thereby maintaining lower diameter values in the central sections and taking increasingly greater diameter values as moving to the end sections. Thereby, the distal and proximal ends of the balloon 1 act as the containment means 20 described above, which are suitable to temporary stop the blood flow in the length involved in the angioplasty operation.

According to a further aspect, the invention relates to a catheter 2 for angioplasty comprising at least one balloon 1 described above.

The method according to the invention for depositing the drug on the balloon 1 as described above, comprises the following steps:

arranging the balloon 1 in a collapsed configuration;
placing a plurality of stylets 17 being arranged in an axial direction between each lap 12 and the core 11 of the balloon 1;
pressing the laps 12 in the radial direction on the core 11 such as to match each lap 12 with the underlying stylet 17;
removing the stylets 17 such as to form a plurality of cavities 13 that are comprised between each lap 12 and the core 11 of the balloon 1;
filling the cavities 13 with a drug 14.

In accordance with a particular embodiment, the step described above of placing the stylets 17 between each lap 12 and the core 11 of the balloon 1, comprises the following steps:

injecting the inflating liquid into the balloon 1 such as to bring the latter in the deployed configuration;
placing a plurality of stylets 17 being arranged in the axial direction along the outer wall 10 of the balloon 1;
pushing the stylets 17 in the radial direction towards the core 11 of the balloon 1 such as to form a plurality of laps 12;
laying the laps 12 in the tangential direction about the core 11 such as to lay each lap 11 on a stylet 17 adjacent thereto;
sucking the inflation liquid from the balloon 1 such as to bring it back to the collapsed configuration thereof.

In accordance with different embodiments of the method, the stylets 17 can have different sections according to the particular requirements. In FIG. 6a to 6d, several possible sections of the stylets 17 are illustrated by way of example.

In accordance with an embodiment of the method, the drug 14 is dripped within the cavities 13 that have formed when the stylets 17 have been removed.

In accordance with several embodiments of the method, the stylets are hollow and are suitable to deliver the drug 14 that is intended to fill the cavities 13. Preferably, during the step of removing the stylets 17, from the end of each stylet 17 a volume of drug 14 is delivered, which is suitable to fill the cavity 13 that will be formed as the stylet is being removed.

In accordance with these embodiments of the method, the stylets 17 have thus a hollow section, unlike what has been illustrated in FIG. 6a to 6d.

In accordance with several embodiments of the method, the drug 14 is sucked within the cavity 13 by applying a suitable depressurization.

In accordance with several embodiments of the method, the drug 14 is arranged at an end of the cavities 13 (such as at the distal end) and is then sucked within the cavities 13 by applying a depressurization at the opposite end (such as at the proximal end).

In any case, the amount of drug 14 being arranged within the cavities 13 has to be adjusted such as to ensure that the proper amount of active ingredient is brought in contact with the vessel wall during the angioplasty operation.

Figure 5:
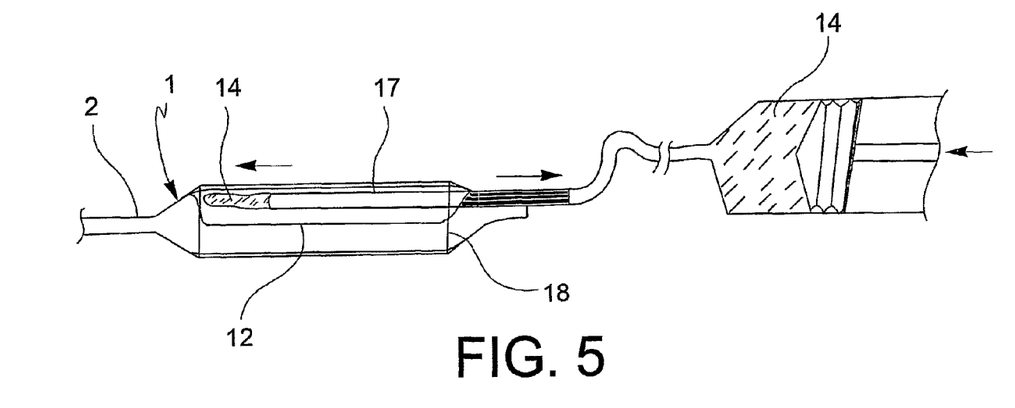
FIG. 5 is a partially sectional side view of an angioplasty balloon during a step of a method according to the invention.
Figure 6:
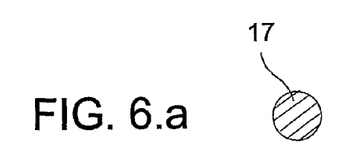

In accordance with several embodiments of the method (see for example FIGS. 4d and 5), during the step of filling the cavities 13 with the drug 14, the balloon 1 is wrapped within a protective sheath 18. The protective sheath 18 has the purpose of keeping the laps 12 in position, such that the drug 14 does not escape from the cavities 13.

From what has been set forth above, those skilled in the art may appreciate how the balloon according to the invention can at least partially overcome the drawbacks of prior art balloons.

In fact, in the balloon according to the invention, when in the collapsed configuration, the drug 14 is protected by the laps 12. In other words, when the balloon 1 is in the collapsed configuration, the drug 14 is not exposed to contact with the external environment, and only the strips 16 of the wall not covered with drug 14 are exposed. This characteristic allows the balloon to be advanced along the vessels of the circulatory system without dispersing the drug intended for the stenosis in healthy districts along the pathway.

It is understood that only some particular embodiments of the balloon and method for manufacturing the same according to the present invention have been described, to which the man skilled in the art shall be able to bring any modifications required to adapt it to particular applications, without however departing from the scope of protection as defined in the claims below.

The invention claimed is:

1. A method for arranging a drug on an angioplasty balloon, the balloon being suitable to adopt a deployed configuration and a collapsed configuration, having an outer wall and a core defining an axis, the balloon comprising in the collapsed configuration a plurality of laps that are laid in the tangential direction about the core, the method comprising:

provide a plurality of stylets arranged in an axial direction between the plurality of laps and the core of the balloon;

pressing the plurality of laps in the radial direction on the core to move the balloon to the collapsed configuration while the plurality of stylets are arranged in the axial direction between the plurality of laps, wherein each stylet of the plurality of stylets comprises an underlying stylet located between each lap of the plurality of laps and the core of the balloon when each lap of the plurality of laps is located in the circumferential direction over the underlying stylet;

removing the stylets from between each lap of the plurality of laps and the core of the balloon after pressing to form a cavity between each lap of the plurality of laps and the core of the balloon;

filling the cavity between each lap of the plurality of laps and the core of the balloon with the drug.

2. The method according to claim 1, wherein the balloon is wrapped in a protective sheath configured to keep the laps in position when filling the cavity between each lap of the plurality of laps and the core of the balloon with the drug.

3. The method according to claim 1 wherein the filling comprises dripping the drug into the cavities that are formed when the stylets are removed.

4. The method according to claim 1, wherein the stylets are hollow and wherein the filling comprises delivering the drug through the hollow stylets.

5. The method according to claim 4, wherein removing the stylets comprises delivering a volume of the drug from an end of each hollow stylet to fill the cavity formed as the hollow stylet is being removed.

6. The method according to claim 1, wherein the drug is sucked within the cavities by applying a depressurization.

7. The method according to claim 1, further comprising fitting a stent on the balloon.

8. The method according to claim 1, further comprising fitting a stent on the balloon.

9. A method for arranging a drug on an angioplasty balloon, the balloon being suitable to adopt a deployed configuration and a collapsed configuration, having an outer wall and a core defining an axis, the balloon comprising in the collapsed configuration a plurality of laps that are laid in a tangential direction about the core, the method comprising:

placing a plurality of stylets arranged in the axial direction along the outer wall of the balloon when the balloon is in the deployed configuration;

pushing the plurality of stylets in the radial direction towards the core of the balloon to form the plurality of laps in the balloon;

laying the plurality of laps in the tangential direction about the core to move the balloon to the collapsed configuration while the plurality of stylets are arranged in in the axial direction along the outer wall of the balloon, wherein each stylet of the plurality of stylets comprises an underlying stylet located between each lap of the plurality of laps and the core of the balloon;

removing the underlying stylets from between each lap of the plurality of laps and the core of the balloon after the laying to form a cavity between each lap of the plurality of laps and the core of the balloon; and filling the cavity between each lap of the plurality of laps and the core of the balloon with the drug.

10. The method according to claim 9, wherein the balloon is wrapped in a protective sheath configured to keep the laps in position when filling the cavity between each lap of the plurality of laps and the core of the balloon with the drug.

11. The method according to claim 9 wherein the filling comprises dripping the drug into the cavities that are formed when the stylets are removed.

12. The method according to claim 9, wherein the stylets are hollow and wherein the filling comprises delivering the drug through the hollow stylets.

13. The method according to claim 12, wherein removing the stylets comprises delivering a volume of the drug from an end of each hollow stylet to fill the cavity formed as the hollow stylet is being removed.

14. The method according to claim 9, wherein the drug is sucked within the cavities by applying a depressurization.

* * * * *